United States Patent [19]

Russell

[11] Patent Number: 5,976,504

[45] Date of Patent: *Nov. 2, 1999

[54] TOPICAL AEROSOL FORMULATION FOR COOLING OF MAMMALIAN TISSUES

[75] Inventor: Julian Paul Russell, Nottingham, United Kingdom

[73] Assignee: The Boots Company, PLC, Nottingham, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/592,302

[22] PCT Filed: Aug. 5, 1994

[86] PCT No.: PCT/EP94/02624

§ 371 Date: Jun. 12, 1996

§ 102(e) Date: Jun. 12, 1996

[87] PCT Pub. No.: WO95/04522

PCT Pub. Date: Feb. 16, 1995

[30] Foreign Application Priority Data

Aug. 10, 1993 [GB] United Kingdom .................... 9316550
Nov. 13, 1993 [GB] United Kingdom .................... 9323487

[51] Int. Cl.⁶ ..................................................... A61K 9/12
[52] U.S. Cl. .......................... 424/45; 424/47; 424/78.02; 424/78.03; 514/817; 514/887
[58] Field of Search ........................... 424/45, 47, 78.03, 424/78.02; 514/887, 817

[56] References Cited

U.S. PATENT DOCUMENTS

| | | |
|---|---|---|
| 3,207,386 | 9/1965 | Presant et al. . |
| 3,694,545 | 9/1972 | Roth . |
| 3,694,546 | 9/1972 | Roth . |
| 4,134,968 | 1/1979 | Stebles . |
| 4,466,838 | 8/1984 | Heeb . |
| 4,584,021 | 4/1986 | Bartlett . |
| 4,597,895 | 7/1986 | Bartlett . |
| 4,600,530 | 7/1986 | Bartlett . |
| 4,716,032 | 12/1987 | Westfall . |
| 5,269,958 | 12/1993 | de Jager . |

FOREIGN PATENT DOCUMENTS

| | | |
|---|---|---|
| 404334 | 12/1990 | European Pat. Off. . |
| 414920 | 3/1991 | European Pat. Off. . |
| 54-032185 | 3/1979 | Japan . |
| 54-086606 | 7/1979 | Japan . |
| 56-135414 | 10/1981 | Japan . |
| 61-209288 | 9/1986 | Japan . |
| 62-029512 | 2/1987 | Japan . |
| 62-033115 | 2/1987 | Japan . |
| 62-205019 | 9/1987 | Japan . |
| 63-258405 | 10/1988 | Japan . |
| 01301618 | 12/1989 | Japan . |
| 03209315 | 9/1991 | Japan . |
| 04007389 | 1/1992 | Japan . |
| 04103526 | 4/1992 | Japan . |
| 413488 | 5/1966 | Switzerland . |
| 2008611 | 6/1979 | United Kingdom . |
| 1578331 | 11/1980 | United Kingdom . |
| 9003166 | 4/1990 | WIPO . |
| 9413753 | 6/1994 | WIPO . |

OTHER PUBLICATIONS

*Aerosol Spray Report*, vol. 31, No. 11, pp. 592–595 –(1992).
*Aerosol Age*, pp. 20–24 and 54–55 (1992).

*Primary Examiner*—Raj Bawa
*Attorney, Agent, or Firm*—Nikaido Marmelstein Murray & Oram, LLP.

[57] ABSTRACT

Aerosol formulations for topical administration for cooling of mammalian tissues. The formulations are rapid onset and sustained effect, and further contain no CFCs and are nonflammable.

21 Claims, 2 Drawing Sheets

TOPICAL AEROSOL FORMULATION FOR COOLING OF MAMMALIAN TISSUES

This invention relates to an aerosol formulation for administration in the form of a spray which has a cooling effect on the tissues to which it is applied.

BACKGROUND OF THE INVENTION

1. Field of the Invention

It is desired to provide an effective cooling aerosol spray formulation which does not contain halo-substituted solvents such as chlorofluorocarbon compounds (CFCs) or chloro-substituted compounds. European Patent Application 404334 seeks to provide such. an aerosol formulation based on organic solvents without CFCs and proposes particular blends of certain petroleum distillates in the formulation. Although such products go some way to satisfy concerns regarding flammability, it is desired to improve the non-flammability properties of the formulations still further, particularly in respect of the residue of the product remaining on the skin after administering the spray.

We have now found that we can provide a water-based aerosol formulation with improved non-flammability properties. The presence of water considerably improves the non-flammability properties and also provides a spray formulation having valuable cooling properties with a fast onset of action combined with a sustained cooling effect. We have overcome the problem of combining the propellant (which is necessary in formulations adapted for aerosol use) in a water-based formulation as a single phase. Thus we have been able to produce a homogeneous mixture including water with dimethyl ether as propellant for aerosol use. The aqueous single phase aerosol spray formulation according to the present invention comprises dimethoxymethane, dimethyl ether and an alcoholic co-solvent. The formulation has been achieved without any halogenated component.

2. Description of the Prior Art

Other aqueous based aerosol formulations have also been proposed, however, they are associated with a number of disadvantages. For example, UK Patent Application 2008611A proposes a self-propellant spray system for use in cosmetics, for room treatment and/or in medicine, comprising a mixture of active compound, carbon dioxide, dimethyl ether, water and either methylene chloride or 1,1,1-trichloroethane. However, this composition still requires the use of chlorinated solvents. Japanese Patent Application No. 56135414 proposes an aerosol type antiinflammatory analgesic formulation comprising as propellants liquid petroleum gas and dimethyl ether and as a liquid phase, specified active ingredients, alcohol and water. However, the cooling effect on the skin is achieved by the selection of three of the particular four active ingredients specified. European Patent Application 414920A proposes a cooling formulation in the form of a sherbet-type foam. This may be messy to use and the cooling effect is much reduced when the foam is applied to dressings covering the affected area. U.S. Pat. No. 4716032 proposes an aqueous-based cooling spray for preventing mastitis in cows comprising a mixture of propellant (such as dimethyl ether), water, a disinfectant and other listed components including a $C_{1-3}$ alkanol and an emollient. However, a satisfactory cooling effect for use in accordance with the present invention would not be achieved due to the high level of water present.

SUMMARY OF THE INVENTION

The present provides an aerosol formulation for administration in the form of a spray to impart a cooling effect comprising:

(a) 5–35% by weight water;
(b) 15–40% by weight dimethoxymethane;
(c) 5–20% by weight alcoholic co-solvent; and
(d) at least 20% by weight dimehyl ether.

The combined fast-onset and sustained cooling effect achieved is particularly valuable for therapy.

The cooling properties of a formulation according to the present invention lead to the alleviation of pain and discomfort of the sufferer in the area to which the formulation is applied, either directly or through a dressing covering the affected area, namely the skin and surrounding tissues. This effect may be particularly utilized in the treatment of soft tissue injuries, including sports injuries, such as bruising and sprains, and also in the alleviation of muscular and rheumatic pain such as back pain, arthritic conditions, stiffness, lumbago, and fibrositis.

The presence of the water in the aerosol formulation according to the present invention significantly reduces the flammability of the formulation. Not only is this seen in the properties of the spray ejected from the aerosol can, but also in the properties of the residue remaining on the skin. The formulation according to the present invention also remains substantially homogeneous on storage. This has the advantage that the aerosol can containing the formulation does not require to be shaken vigorously before each use to ensure that all the components of the formulation are dispensed together. The uniform mix of components ensures that substantially all the formulation is expelled from the container. Otherwise, when the propellant is exhausted, the remaining formulation cannot be dispensed from the aerosol can.

In a formulation according to the present invention, the dimethyl ether is preferably used to an extent of 20–70% by weight, more preferably 30–60% by weight and most preferably 35–55% by weight of the formulation. Dimethyl ether primarily acts as a propellant. However, when combined with the other components in the spray it has been found to have a valuable initial cooling effect on the skin.

In a formulation according to the present invention, the water may be de-ionised, for example to prevent corrosion of the aerosol container in which the formulation is contained. Preferably water is used in an amount of 10–30% by weight, more preferably 15–25% by weight of the formulation. The water contributes significantly to the cooling effect of the spray and, in particular, provides a valuable sustained cooling effect. The use of water in the formulation not only significantly reduces the flammability of the product but also, in replacing the organic solvent normally used in such formulations, reduces solvent emission to the atmosphere.

In a formulation according to the present invention, the dimethoxymethane is preferably used in an amount of 16–30% by weight, more preferably 17–25% by weight of the formulation. The dimethoxymethane has valuable cooling properties, particularly being effective after the initial cooling effect of the dimethyl ether and before the cooling effect of the water is felt. The dimethoxymethane component also aids the formation of a homogeneous mixture between the dimethyl ether and water.

In a formulation according to the present invention, the alcoholic co-solvent aids the miscibility of the dimethyl ether, the water and the dimethoxymethane. Preferably, it is a lower alkanol such as a $C_{1-6}$ alkanol. More preferred examples include $C_{1-4}$ alkanols such as ethanol, isopropanol, n-propanol and isobutananol, especially ethanol and isopropanol. Preferably, lower alcohols may be used in an amount of 5–15% by weight, more preferably 6–10% by weight of the formulation. Lower glycols may also be used as a co-solvent in accordance with the present invention. Suitable $C_{1-6}$ glycols include propylene glycol, dipropylene glycol, ethylene glycol, triethylene glycol and butylene glycol. Such glycols are preferably used in an amount of 10–20% by weight, preferably 10–15% by weight of the formulation.

In preferred formulations according to the present invention the ratio of water (component (a)) to dimethyl ether (component (d)) is in the range 1:1 to 1:4 parts by weight, preferably 1:1 to 1:2.5 parts by weight and more preferably 1:2 to 1:2.5 parts by weight. In further preferred formulations the ratio of water (component (a)) to the dimethoxymethane/co-solvent combination (components (b) and (c)) is 1:0.5 to 1:2 parts by weight, preferably 1:1 to 1:2 parts by weight, and more preferably 1:1 to 1:1.5 parts by weight.

The spray formulation according to the present invention may contain only the four components specified above. However, it may also contain other formulation ingredients as desired. For example it may contain 0.01–2% by weight of one or more corrosion inhibitors, such as sodium benzoate, sodium nitrite or sodium succinate. Other ingredients may include a non-steroidal anti-inflammatory agent such as ibuprofen, flurbiprofen, acetylsalicylic acid, methyl salicylate, ketoprofen, naproxen or, in cases where there is a chiral centre, the (+)-enantiomers of these active ingredients. Such ingredients are employed in an analgesically effective amount of the formulation. Further ingredients may include a rubifacient (eg ethyl nicotinate) in a amount of 0–2%, further cooling ingredients (eg menthol) in an amount of 0–2% and perfumes and skin conditioning agents in an amount of 0–5%.

One commercial source of dimethoxymethane is Lambiotte et Cie S.A., Avenue des Aubépines 18, Brussels, Belgium, under the trade name Methylal (Registered Trade Mark). Methylal is defined as containing greater than 99.5% w/w dimethoximnethane, less than 1 part per million methanol, less than 1 part per million formaldehyde and less than 0.5% w/w water.

The formulation according to the present invention is arranged to be dispensed from an aerosol can. It therefore contains a sufficient amount of propellant to allow the formulation to be expelled through a valve of the aerosol can. The formulation is thus administered in the form of a spray onto the affected tissues.

Accordingly, in another aspect the invention provides an aerosol can containing a formulation specified herein. Said combination is for use in obtaining a cooling effect on the skin and surrounding tissues to which the spray is applied.

The aerosol can uses a valve type adapted to produce a spray which has a cooling effect when a formulation according to the present invention is dispensed therethrough. We prefer not to use fine sprays as the cooling effect may not be fully achieved. Standard aerosol valves commonly provide spray rates in the range 0.4–2.0 $gs^{-1}$, depending on the formulation type used in the can; other valves may produce a higher spray rate. Such valves may be suitable for use in accordance with the present invention. Preferably, the cooling effects of a formulation according to the present invention are achieved by ensuring that the spray rate of the formulation applied to the affected tissues is 1 $gs^{-1}$ or more. An increase in spray rate will increase the cooling effect, as it reduces the extent to which the volatile dimethyl ether (boiling point −25° C.) evaporates before contact with the skin. As outlined above the dimethyl ether provides a beneficial initial cooling effect. The maximum spray rate may be defined by the valve used. The greater spray rate, the greater amount of formulation expelled. The spray rate may be determined by the British Aerosol Manufacturers Association (BAMA) Standard, Measurement of Aerosol Discharge Rate, in which the weight loss in a five second discharge at 25° C. is measured. A preferred spray rate is in the range 1–4 $gs^{-1}$, more preferably 1.5–3 $gs^{-1}$.

Factors affecting the spray rate include the characteristics of the aerosol can components from which the formulation is dispensed (in particular orifices in the valve assembly of the can through which the formulation passes) as well as the nature of the formulation itself. In the can there is a lower liquid single phase comprising the ingredients a) to d) specified hereinabove and an upper vapour phase comprising propellant vapour. As described hereinafter, the can comprises a container holding the liquid formulation and an actuator through which the spray is dispensed. The actuator is connected to the container via a valve assembly. The valve assembly controls the way in which the product is dispensed, including the spray race. The valve assembly includes a valve housing, a restricted tail piece connecting the valve housing with the liquid phase in the container via a dip-tube and a stem portion connecting the valve housing with the actuator. The restricted tail Niece includes an orifice through which the liquid phase is introduced into the valve housing via the dip-tube from a lower portion of the container. The valve housing may also include a vapour phase tap through which the vapour phase is introduced into the valve housing from an upper portion of the container. The liquid optionally together with vapour passes out of the valve housing through a stem orifice of the stem portion into the stem. The formulation is then dispensed through an orifice in the actuator in the form of a spray.

The vapour phase tap is an optional feature as the liquid phase may pass through the valve housing and through the stem into the actuator without being mixed with the vapour phase. We prefer not to include a vapour phase tap in a valve housing in accordance with the present invention.

Thus, factors affecting the spray rate will include the size of:

(a) the restricted tail piece orifice;
(b) the optional vapour phase tap;
(c) the stem orifice; and
(d) the actuator orifice.

An increase in the size of the restricted tail piece orifice will increase the spray rate as more liquid phase is allowed into the valve housing compared with a smaller orifice. Preferred restricted tail piece orifices have a diameter in the range 0.4–2.5 mm, more preferably 0.7–2.1 mm.

Reducing the size of the vapour phase tap or omitting it altogether increases the spray rate as the dilution of the liquid concentrate with vapour is reduced compared with a larger orifice. Preferred vapour phase tap orifices have a diameter of up to 0.5 mm, for example 0.3–0.5 mm. As noted hereinabove, we prefer not to use a vapour phase tap.

The greater the size of the stem orifice the greater the spray rate as the phase or phases pass therethrough at a higher rate compared with a smaller orifice. Preferred stem orifices have a diameter 0.3–1.1 mm, more preferably 0.4–0.8 mm, most preferably 0.4–0.6 mm. It is also possible to have up to four stem orifices in one valve assembly. The greater the number of stem orifices the higher the spray rate. We prefer to use one or two stem orifices in a valve assembly used in accordance with the present invention.

The greater the actuator orifice the greater the size of the spray particles as a small orifice acts to break up the spray. The greater the size of the actuator orifice, the greater the spray rate. Preferred actuator orifices have a diameter 0.3–1.1 mm.

Some actuators may include mechanical break-up channels located immediately in front of the actuator orifice through which the spray is dispensed. Small channels cause turbulence of product as it passes therethrough which causes break up of the particles as they hit the actuator orifice thus leading to a finer spray. It is preferred to have a directional spray in accordance with the present invention. Preferred average particle sizes of sprays are in the range 10–150 µm, more preferably 15–90 µm.

Other factors affecting spray rate and size include the proportion of propellant in the formulation. Increasing the amount of dimethyl ether increases the spray rate compared to a lower amount of propellant as the pressure in the can urging the formulation up the stem and through the actuator orifice is higher. In addition the particle size is increased when the viscosity of the formulation is increased. The nature of the housing surrounding the actuator orifice also determines the spray rate, for example standard actuator orifices and barrel nose actuator orifices are examples of suitable types. The barrel nose includes a small extension tube through which the spray is dispensed after the liquid and vapour phases pass through the actuator orifice. The barrel nose concentrates the spray into a jet, hence increasing the amount of liquid coming into contact with the skin, therefore improving the efficacy of the product.

The invention further provides an aerosol spray formulation comprising:

(a) 5–35% water (b) 15–40% dimethoxymethane (c) 5–20% alcoholic co-solvent (d) at least 20% by weight dimethyl ether for use in obtaining a cooling effect on the skin and surrounding tissues to which the spray is applied.

In a preferred use as described above, the spray is used at a spray rate of at least 1 gs$^{-1}$.

A formulation according to the present invention may be for human or veterinary use and applied to the site of injury as often as necessary to maintain a cooling effect. The spray may be applied to the treatment site directly or may be applied to a dressing covering the site of treatment. Accordingly in another aspect, the present invention further provides a method of cooling mammalian tissues comprising the topical administration of an aerosol formulation comprising:

(a) 5–35% water (b) 15–40% dimethoxymethane (c) 5–20% alcoholic co-solvent (d) at least 20% by weight dimethyl ether, in the form of a spray.

In a preferred method as described above the spray is administered to the affected tissues at a spray rate of at least 1 gs$^{-1}$, preferably 1–4 gs$^{-1}$, most preferably 1.5–3 gs$^{-1}$.

In another aspect, the present invention provides a method for alleviating pain associated with an injury sustained on the skin and surrounding tissues comprising the topical administration of a spray formulation as described herein. Preferably, the spray is administered at a spray rate of 1–4 gs$^{-1}$.

The water, dimethoxymethane and co-solvent are all liquid at room temperature. The dimethyl ether is gaseous at room temperature but liquefies under pressure in the aerosol can. The formulation according to the present invention may be prepared by mixing components (a), (b) and (c) together with optional ingredients, filling into an aerosol container and then adding the dimethyl ether as the propellant through the valve assembly according to known methods in aerosol technology. Most of the propellant liquefies and forms a single phase with components (a), (b) and (c). Alternatively, the water and ethanol may be combined and filled into the aerosol container; the dimethoxymethane is then introduced into the container, such as through the valve and finally the dimethyl ether is added through the valve. A very small proportion (by weight) of the propellant remains as a vapour phase in the upper portion of the can. As the can is emptied, a small amount of dimethyl ether (by weight) is transferred from the liquid to the vapour phase. when defined herein the formulation according to the present invention refers to the liquid phase contained within the can which is for administration in the form of a spray.

The invention is illustrated by the following non-limitative Examples.

There now follows a detailed description to be read with reference to the accompanying drawing of an aerosol can suitable for use with a formulation according to the present invention. It will be realised that these embodiments have been selected for description to illustrate the invention by way of example only.

DESCRIPTION OF THE PREFERRED EMBODIMENTS

Figure 1:
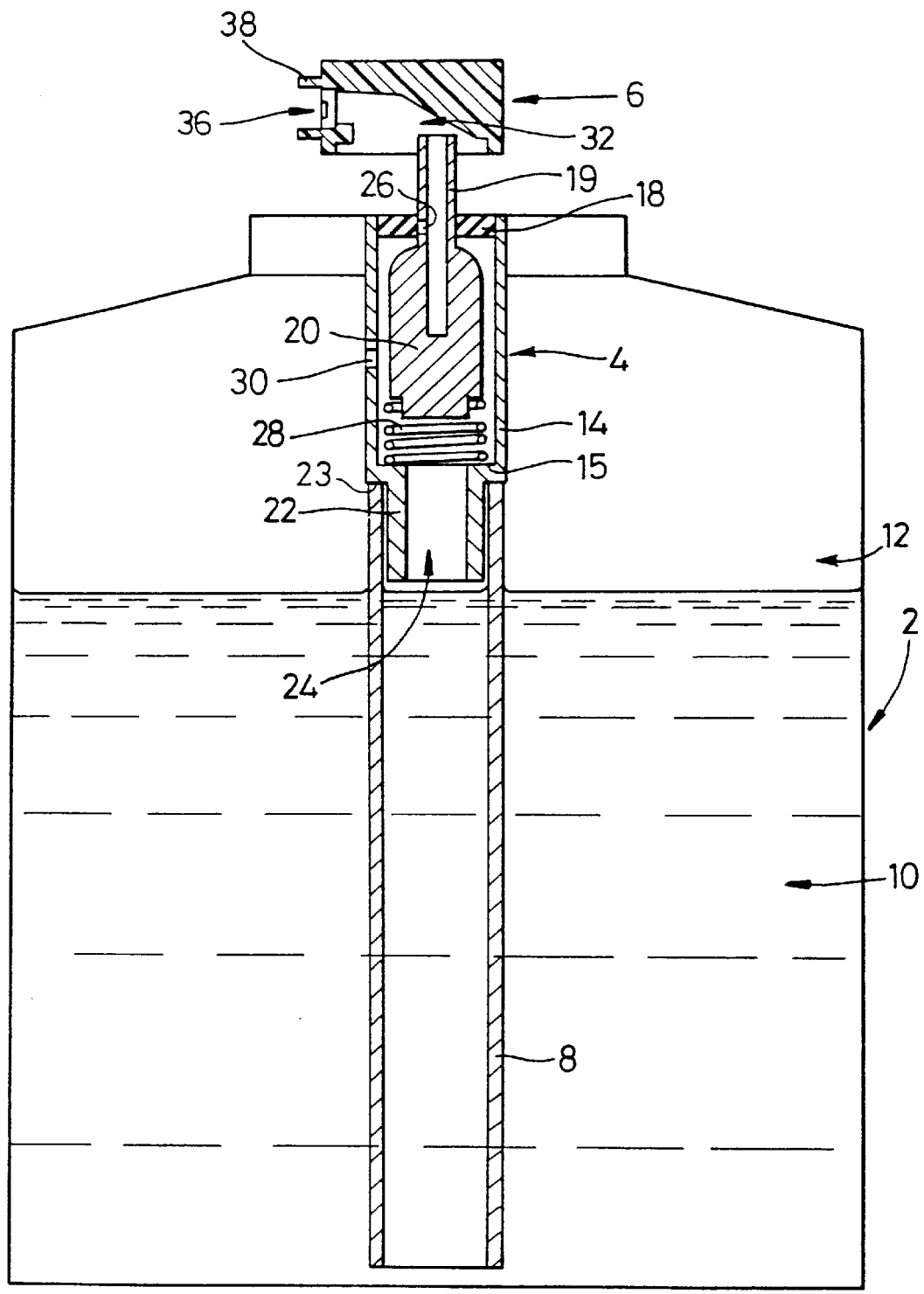
FIG. 1 is a sectional view of an aerosol can when not in use.
Figure 2:
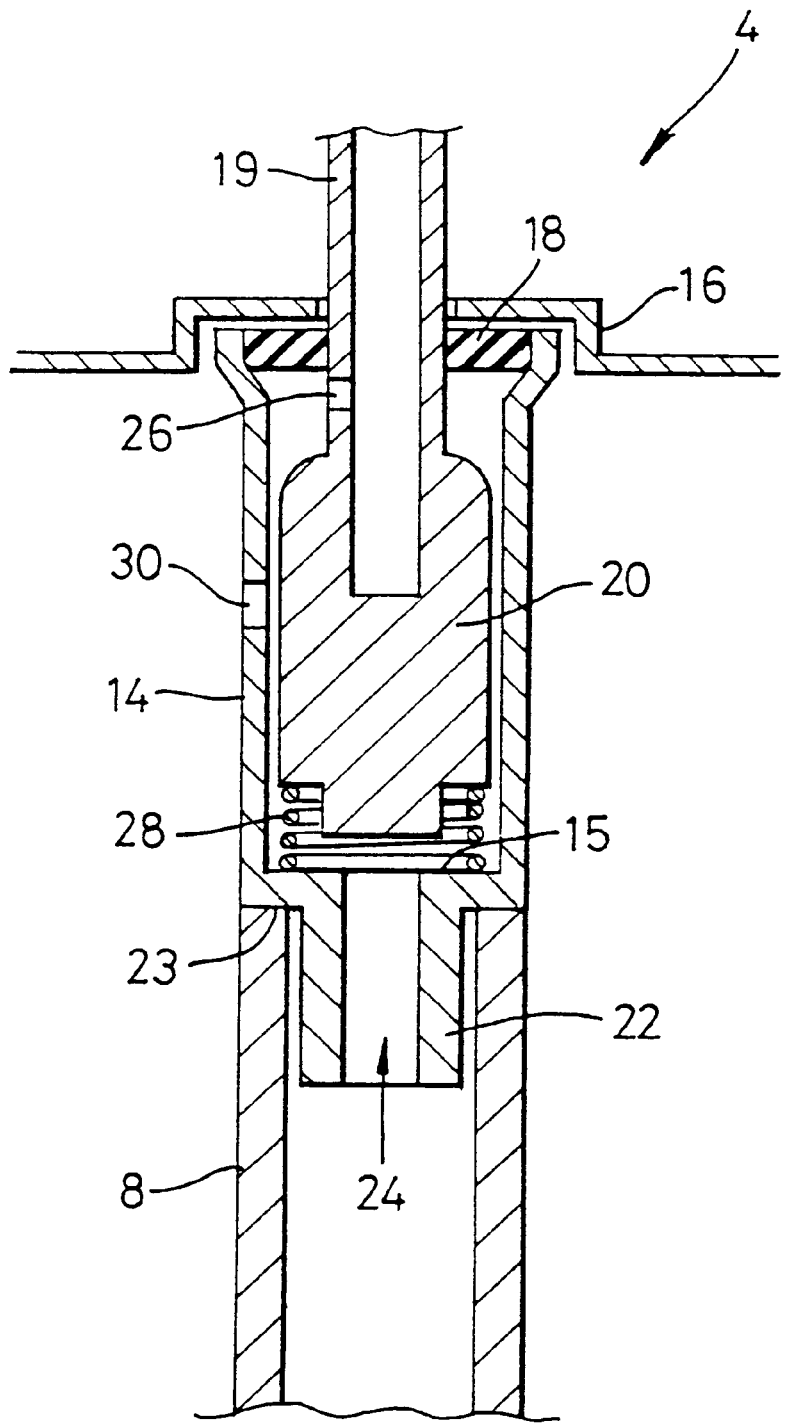
FIG. 2 is an enlarged sectional view of a valve assembly of an aerosol can when in use.

The aerosol can comprises a container 2, a valve assembly 4, an actuator 6 and a dip-tube 8. The liquid formulation initially fills the container 2 to an extent of approximately ⅔ of the volume of the container. The liquid formulation according to the invention forms a liquid phase 10 in a lower portion of She container. An upper portion of the container contains a vapour phase 12 of propellant. The valve assembly comprises a stem portion 20 and a valve housing 14 which has a restricted tail piece 22 at a lower end. The restricted tail piece is received within the end of the dip-tube 8 such that the dip-tube abuts a shoulder 23 of the valve housing 14. The dip-tube 8 extends almost to the base of the container 2 and is arranged so that the liquid phase is drawn from the container 2 up through the dip-tube 8, through an orifice 24 (diameter 2.0 mm) of the restricted tail piece 22 and into the valve housing 14. The valve housing 14 also comprises a vapour phase tap 30 (diameter 0.51 mm) which is an orifice located in the side of the valve housing through which tap the vapour phase 12 may be introduced into the valve housing 14 from the container 2. The stem portion 20 mounted on a spring 28 is received within the valve housing 14 and rests on an internal shoulder 15. The stem portion 20 connects the valve assembly 4 with the actuator 6. A stem 19 of the stem portion 20 passes through an aperture in a neck (valve cup) 16 of the can. The stem 19 is arranged for slidable movement through a gasket 18. The gasket 18 acts to seal a stem orifice 26 of the stem 19 when the aerosol can is not in use. When the stem orifice 26 is unsealed by being moved downwardly of the gasket 18 the liquid and vapour phases pass from the valve housing through the stem orifice 26 (diameter 0.51 mm) and into the stem 19 of the stem portion 20. The phases then pass into the actuator 6 which comprises a chamber 32, an actuator orifice 36 and a barrel nose 38.

When it is desired to apply an Example formulation (as illustrated hereinafter) to cool an affected area of a person requiring treatment, the actuator 6 is depressed causing the stem portion 20 mounted on the spring 28 to be depressed thus unsealing the stem orifice 26. When the stem orifice is unsealed vapour phase 12 admixed with liquid phase 10 is drawn through the stem orifice 26 into the stem 19. Further liquid phase 10 is drawn up through the dip-tube 8 from the container 2, through the restricted tail piece orifice 24 and into the valve housing 14. Vapour phase 12 entering the valve housing 14 through the vapour phase tap 30 mixes with the liquid phase 10 and both phases pass together through the stem orifice 26 into the stem 19. The mixture of liquid phase and vapour phase enters the chamber 32 of the actuator and then is expelled from the actuator through the actuator orifice 36 and barrel nose 38.

In a second embodiment, the vapour phase tap 30 is absent. In use, when the stem orifice 26 is unsealed by depression of the actuator, the liquid phase 10 passes into the valve housing 14. It further passes through the stem orifice 26 into the stem 19 and out of the actuator as hereinbefore described. Further liquid phase in then drawn up through the dip-tube 8 into the valve housing 14. The spray rate is increased compared to the first embodiment.

In a third embodiment both the vapour pressure tap 30 and the barrel nose 38 are absent and the valve housing 14 includes two stem orifices 26. The spray rate is increased compared to either of the first or second embodiments.

Each of the following Example compositions (1–4 and 5–10) were prepared by mixing water, dimethoxymethane and ethanol together, filling into an aerosol can, sealing the can with the provision of an appropriate valve assembly and then adding the dimethyl ether as propellant through the valve according to known methods in aerosol technology.

| | EXAMPLE | | | |
|---|---|---|---|---|
| | 1 | 2 | 3 | 4 |
| Water | 26 | 18 | 23 | 13 |
| Dimethoxymethane | 17 | 25 | 20 | 30 |
| Ethanol | 7 | 7 | 7 | 7 |
| Dimethyl ether | 50 | 50 | 50 | 50 |

| | EXAMPLE | | | | | |
|---|---|---|---|---|---|---|
| | 5 | 6 | 7 | 8 | 9 | 10 |
| Water | 20 | 27 | 19 | 12 | 20 | 23 |
| Dimethoxymethane | 36 | 17 | 24 | 31 | 19 | 36 |
| Ethanol | 6 | 6 | 7 | 7 | 11 | 7 |
| Dimethyl ether | 38 | 50 | 50 | 50 | 50 | 34 |

The Example aerosol formulations were presented in an aerosol can with a standard valve (restricted tail piece orifice 2.0 mm; stem orifice 0.51 mm; actuator orifice 1.04 mm; no vapour phase tap) adapted to provide a spray rate of $1-3\ gs^{-1}$ as measured by the BAMA standard noted hereinabove.

Each formulation was found to have good cooling properties.

Each formulation was also found to have acceptable flammability properties, for example as measured by the flame extension (the distance the flame travels when the aerosol is sprayed into a candle from 15 cm), flash-back (the distance the flame burns back towards the aerosol from the candle), self-sustaining nature (whether the spray still burns after it has been removed from the flame or does not burn and ignition distance (the distance from a candle from which the aerosol spray will just ignite).

I claim:

1. A method of cooling mammalian tissues, comprising topically administering to mammalian tissues in need thereof a homogenous single-phase aerosol formulation in the form of a spray consisting essentially of
   (a) 10–30% water,
   (b) 15–40% dimethoxymethane,
   (c) 5–20% alcoholic co-solvent, wherein the alcoholic co-solvent is a lower alkanol, and
   (d) 20–70% by weight dimethyl ether, the ratio of water to dimethylether being in the range of 1:1 to 1:4 parts by weight;
   either directly or through a dressing.

2. The method according to claim 1, wherein the ratio of water to dimethyl ether in the aerosol formulation is in the range of 1:1 to 1:2.5 parts by weight.

3. The method according to claim 1, wherein for each part by weight of water in the formulation there is 1 to 2 parts by weight of dimethoxymethane in combination with the alcoholic co-solvent.

4. The method according to claim 1, wherein the formulation comprises 35–55% by weight of dimethyl ether.

5. The method according to claim 1, wherein the formulation comprises 15–25% by weight of water.

6. The method according to claim 1, wherein the formulation comprises 7–25% by weight of dimethoxymethane.

7. The method according to claim 1, wherein the formulation comprises 5–15% by weight of a $C_{1-4}$ alkanol as the alcoholic co-solvent.

8. The method according to claim 1, wherein the alcoholic co-solvent is ethanol or isopropanol.

9. The method according to claim 1, wherein the formulation is topically administered to the mammalian tissues at a spray rate of $1-4\ gs^{-1}$.

10. The method according to claim 9, wherein the formulation is topically administered to the mammalian tissues at a spray rate of $1.5-3\ gs^{-1}$.

11. A method of alleviating pain associated with an injury sustained on a mammalian skin and tissues underneath the skin layer in the area of injury, comprising topically administering to mammalian skin in need thereof a homogenous single-phase aerosol formulation in the form of a spray consisting essentially of
    (a) 10–30% water,
    (b) 15–40% dimethoxymethane,
    (c) 5–20% alcoholic co-solvent, wherein the alcoholic co-solvent is a lower alkanol, and
    (d) 20–70% by weight dimethyl ether, the ratio of water to dimethylether being in the range of 1:1 to 1:4 parts by weight;
    at a spray rate of $1-4\ gs^{-1}$.

12. The method according to claim 11, wherein the pain arises out of or is associated with at least one of the following conditions: soft tissue injuries, muscular pain and rheumatic pain.

13. The method according to claim 11, wherein the aerosol formulation is topically administered at a spray rate of $1.5-3\ gs^{-1}$ to the skin of a subject having a bruise or a sprain in the area of the bruise or the sprain.

14. The method according to claim 11, wherein the ratio of water to dimethyl ether in the aerosol formulation is in the range of 1:1 to 1:2.5 parts by weight.

15. The method according to claim 11, wherein for each part by weight of water in the formulation there is 1 to 2 parts by weight of dimethoxymethane in combination with the alcoholic co-solvent.

16. The method according to claim 11, wherein the formulation comprises 35–55% by weight of dimethyl ether.

17. The method according to claim 11, wherein the formulation comprises 15–25% by weight of water.

18. The method according to claim 11, wherein the formulation comprises 17–25% by weight of dimethoxymethane.

19. The method according to claim 11, wherein the formulation comprises 5–15% by weight of a $C_{1-4}$ alkanol as the alcoholic co-solvent.

20. The method according to claim 19, wherein the alcoholic co-solvent is ethanol or isopropanol.

21. The method according to claim 12, wherein the formulation is topically administered to the mammalian skin at a spray rate of 1.5–3 $gs^{-1}$.

* * * * *